United States Patent
Le-Khac et al.

(10) Patent No.: US 7,528,269 B2
(45) Date of Patent: May 5, 2009

(54) PROCESS FOR OXIDIZING ORGANIC COMPOUNDS

(75) Inventors: Bi Le-Khac, West Chester, PA (US); Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 365 days.

(21) Appl. No.: 11/312,036

(22) Filed: Dec. 20, 2005

(65) Prior Publication Data

US 2007/0142651 A1 Jun. 21, 2007

(51) Int. Cl.
*C07D 301/12* (2006.01)

(52) U.S. Cl. ..................................................... 549/531

(58) Field of Classification Search ................... 549/531
See application file for complete search history.

(56) References Cited

U.S. PATENT DOCUMENTS

| | | | | |
|---|---|---|---|---|
| 4,428,923 | A | | 1/1984 | Kunkel et al. ............... 423/588 |
| 4,772,458 | A | * | 9/1988 | Gosser et al. ............... 423/584 |
| 4,833,260 | A | * | 5/1989 | Neri et al. ................... 549/531 |
| 5,824,622 | A | | 10/1998 | Harmer et al. .............. 502/407 |
| 5,846,898 | A | | 12/1998 | Chuang et al. .............. 502/181 |
| 5,961,948 | A | | 10/1999 | Wanngård ................... 423/584 |
| 6,156,245 | A | | 12/2000 | Takebayashi et al. ........ 264/4.7 |
| 6,168,775 | B1 | | 1/2001 | Zhou et al. .................. 423/584 |
| 6,284,213 | B1 | | 9/2001 | Paparatto et al. ............ 423/403 |
| 6,375,920 | B2 | | 4/2002 | Fischer et al. ............... 423/584 |
| 6,524,547 | B1 | | 2/2003 | Nyström et al. ............. 423/588 |
| 6,649,140 | B2 | | 11/2003 | Paparatto et al. ............ 423/584 |
| 6,888,013 | B2 | | 5/2005 | Paparatto et al. ............ 549/532 |
| 2003/0215383 | A1 | | 11/2003 | Escrig et al. ................. 423/584 |
| 2004/0151658 | A1 | | 8/2004 | Escrig et al. ................. 423/584 |
| 2004/0184983 | A1 | | 9/2004 | Paparatto et al. ............ 423/584 |
| 2005/0201925 | A1 | | 9/2005 | Le-Khac et al. ............. 423/584 |
| 2005/0202957 | A1 | | 9/2005 | Grey et al. ................... 502/66 |
| 2005/0203304 | A1 | | 9/2005 | Le-Khac et al. ............. 549/531 |

FOREIGN PATENT DOCUMENTS

| BE | 1001038 A7 | 6/1989 |
|---|---|---|
| EP | 0498166 A1 | 1/1992 |

OTHER PUBLICATIONS

G. Centi and F. Trifiro', Ed., *New Developments in Selective Oxidation* 33, 1990.
S. Kobayashi et al., *Chem. Commun.* (2003) 449.
R. Akiyama et al., *Angew. Chem. Int. Ed.* 40 (2001) 3469.
S. Kobayashi et al., *J. Am. Chem. Soc.* 120 (1998) 2985.
F. Helfferich, *Ion Exchange*, McGraw-Hill Book Company, (1962) 26.
R. Albright, "Basic Principles of Catalysis by Functionalized Porous Organic Polymers" in *Catalyst Supports and Supported Catalysts* (1987), A. B. Stiles, Ed., 159.
M. Donbrow, Ed., *Microcapsules and Nanoparticles in Medicine and Pharmacy* 1, 1992.
G. Beestman, "Microencapsulation of Solid Particles" in *Controlled-Release Delivery Systems for Pesticide* (1999), H. Scher, Ed., 31.
C. Ramarao et al., *Chem. Commun.* (2002) 1132.
S. Ley et al., *Chem. Commun.* (2002) 1134.
J. Yu et al., *Chem. Commun.* (2003) 678.
H. Kage et al., *Advanced Powder Technol.* 13 (2002) 265.
N. Zhou et al., *Applied Catalysis A: General* 250 (2003) 239.
R. Szostak, "Non-aluminosilicate Molecular Sieves" in *Molecular Sieves: Principles of Synthesis and Identification* (1989), Van Nostrand Reinhold, 205.
G. Vayssilov, *Catal. Rev.—Sci. Eng.* 39(3) (1997) 209.

* cited by examiner

*Primary Examiner*—Taylor Victor Oh
(74) *Attorney, Agent, or Firm*—Yuanzhang Han

(57) ABSTRACT

This invention is a process for oxidizing an organic compound with a hydrogen peroxide solution produced by reacting hydrogen and oxygen in the presence of an oxidation catalyst. The hydrogen peroxide is produced by reacting hydrogen and oxygen in a solvent in the presence of a $H_2O_2$-producing catalyst comprising a polymer-encapsulated combination of a noble metal and an ion-exchange resin. Polymer encapsulation of the $H_2O_2$-producing catalyst improves its productivity in making hydrogen peroxide and is expected to reduce metal loss.

14 Claims, No Drawings

PROCESS FOR OXIDIZING ORGANIC COMPOUNDS

FIELD OF THE INVENTION

The invention relates to a process for oxidizing organic compounds with hydrogen peroxide. The hydrogen peroxide is produced by reacting hydrogen and oxygen.

BACKGROUND OF THE INVENTION

Hydrogen peroxide is an important intermediate chemical useful in such applications as water treatment, pulp and paper bleaching, and organic synthesis. At present, the commercial process for producing hydrogen peroxide involves anthraquinone autooxidation (see, e.g., U.S. Pat. Nos. 4,428,923 and 6,524,547). The process requires numerous reaction and purification sections, uses a large volume of solvent, and provides a less-than-ideal yield of hydrogen peroxide.

Hydrogen peroxide can also be made by a direct reaction of hydrogen and oxygen in the presence of a suitable catalyst. Known methods of making hydrogen peroxide from hydrogen and oxygen use supported transition metals (Group 3 to 12 elements), especially platinum group metals. A wide variety of inorganic and organic supports have been identified, including activated carbon (see, e.g., U.S. Pat. Nos. 6,168,775 and 6,649,140), fluorinated carbon (see, e.g., U.S. Pat. No. 5,846,898), sulfonic acid-functionalized carbon (see, e.g., U.S. Pat. No. 6,284,213), silica, alumina (see, e.g., U.S. Pat. No. 5,961,948), polymer fiber (see, e.g., U.S. Pat. No. 6,375,920), and ion-exchange resin (see, e.g., U.S. Appl. Pub. No. 2003/0215383).

Hydrogen peroxide is an attractive oxidizing agent in the chemical industry because water is the only byproduct. For example, the oxidation of alkanes, arenes, olefins with hydrogen peroxide in the presence of a titanium zeolite has been demonstrated (see *New Developments in Selective Oxidation*, G. Centi and F. Trifiro, Ed., pp. 33-38). Hydrogen peroxide solutions prepared from the reaction of hydrogen and oxygen may be used (see, e.g., U.S. Pat. Nos. 6,284,213 and 6,888,013; U.S. Appl. Pub. No. 2004/0151658).

Recently, a technique called "microencapsulation" was used to prepare catalysts with improved properties, as reviewed in recent publications (*Chem. Commun.* (2003) 449 and references cited therein; *Angew. Chem., Int. Ed.* 40 (2001) 3469; *J. Am. Chem. Soc.* 120 (1998) 2985; U.S. Appl. Pub. Nos. 2005/0201925, 2005/0202957, and 2005/0203304). EP 0 498 166 A1 discloses an alumina-supported Pd catalyst impregnated with 4-bromostyrene or styrene that is subsequently polymerized (see Example 7 and Comparative Example 8). The poly(4-bromostyrene)-coated catalyst is active in generating hydrogen peroxide from hydrogen and oxygen. U.S. Appl. Pub. No. 2004/0184983 describes a catalyst consisting of: (a) one or more metals of the platinum group as active components; (b) one or more polyolefins; and (c) a carrier. The polyolefin is dissolved in a solvent, and the resulting solution is used to impregnate the carrier or the catalyst. The catalyst is useful in producing hydrogen peroxide from hydrogen and oxygen in a reaction solvent containing halogenated and/or acid promoters.

SUMMARY OF THE INVENTION

The invention is a process comprising reacting hydrogen and oxygen in a solvent in the presence of a $H_2O_2$-producing catalyst to obtain a hydrogen peroxide solution. The $H_2O_2$-producing catalyst comprises a polymer-encapsulated combination of a noble metal and an ion-exchange resin. The process also comprises reacting an organic compound with the hydrogen peroxide solution in the presence of an oxidation catalyst to obtain an oxygenated product. Polymer encapsulation of the $H_2O_2$-producing catalyst improves its productivity and is expected to reduce metal loss during use.

DETAILED DESCRIPTION OF THE INVENTION

The process comprises a $H_2O_2$-producing step and an oxidation step. The $H_2O_2$-producing step comprises reacting hydrogen and oxygen in a solvent in the presence of a $H_2O_2$-producing catalyst comprising a polymer-encapsulated combination of a noble metal and an ion-exchange resin to obtain a hydrogen peroxide solution. The oxidation step comprises reacting an organic compound with the hydrogen peroxide solution in the presence of an oxidation catalyst to obtain an oxygenated product.

$H_2O_2$-Producing Step

A $H_2O_2$-producing catalyst is employed in the process. The $H_2O_2$-producing catalyst comprises a noble metal. Suitable noble metals include gold, silver, platinum, palladium, iridium, ruthenium, osmium, rhenium, and mixtures thereof. Preferred noble metals are Pd, Pt, Au, Re, Ag, and mixtures thereof. While any of the noble metals can be utilized, either alone or in combination, palladium and gold are particularly desirable. Typically, the amount of noble metal present in the catalyst will be in the range of from 0.01 to 20 weight percent (wt. %), preferably 0.1 to 5 wt. %. The manner in which the noble metal is incorporated into the catalyst is not critical. For example, the noble metal may be supported on the ion-exchange resin by impregnation, ion exchange, adsorption, precipitation, or the like.

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium(0)).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being introduced into the catalyst may be fully or partially pre-reduced. Satisfactory catalytic performance can, however, be attained without any pre-reduction.

The $H_2O_2$-producing catalyst also comprises an ion-exchange resin as a support. Ion-exchange resins are synthetic organic polymers having ion-exchange properties. Examples of ion-exchange resins can be found in *Ion Exchange*, Friedrich Helifferich, McGraw-Hill Book Company, Inc. (1962), pp. 26-71. Preferably the ion-exchange resin is crosslinked. Ion-exchange resins are categorized according to functionality as either strong or weak acids or bases. Acidic resins (cationic resins) generally contain sulfonic acid or carboxylic acid groups. Basic resins (anionic resins) generally contain amine, substituted amine, ammonium, or substituted ammonium groups. Particularly preferred resins include the addition copolymers prepared from vinyl monomers.

Although gelular ion-exchange resins can be used, macroreticular ion-exchange resins are preferred (see F. Helfferich, *supra.* pp. 59-60). Macroreticular resins consist of agglomerates of very small gelular microspheres. They have both micropores and micropores. The average pore diameter of the resin is preferably greater than 10 angstroms (Å), more preferably greater than 20 Å. The internal surface area of the resin is typically in the range of 1-1000 square meters per gram ($m^2/g$), preferably in the range of 10-900 $m^2/g$, more preferably in the range of 30-600 $m^2/g$ (see R. L. Albright, "Basic Principles of Catalysis by Functionalized Porous Organic Polymers," *Catalyst Supports and Supported Catalysts* (1987) A. B. Stiles, Ed., Butterworths Publishers, pp. 159-186).

Preferably, an acidic resin (cationic resin) is used. Particularly preferred resins are sulfonic acid polystyrene resins, i.e., crosslinked polystyrene containing sulfonic acid functional groups. Divinylbenzene is commonly used as the crosslinking agent. When an acidic ion-exchange resin is used, its protons may be partially exchanged by other cations. Suitable cations include alkali metal, alkaline earth metal, lanthanide metal, zinc, cadmium, ammonium, alkylammonium, alkylphosphonium ions, and the like, and mixtures thereof.

The capacity of the ion-exchange resin is not critical. The capacity is a measure of the concentration of the functional groups (e.g., sulfonic acid or carboxylic acid, amine, ammonium, substituted ammonium) in the resin. Suitable ion-exchange resins may contain 0.01-20 equivalents per kilogram (eq/kg) of functional groups. Preferred resins contain 0.1-15 eq/kg; particularly preferred resins contain 1-10 eq/kg. For example, Amberlyst 36 (an acidic resin available from Rohm & Haas) contains 5.4 eq/kg of sulfonic acid groups.

The $H_2O_2$-producing catalyst may contain other components, e.g., titania, zirconia, niobia, silica, alumina, silica-alumina, titania-silica, zirconia-silica, niobia-silica, and the like, and mixtures thereof. A composite of an ion-exchange resin and any of the above components may also be used as a support for the catalyst. For instance, U.S. Pat. No. 5,824,622 discloses porous microcomposites comprising a perfluorinated ion-exchange polymer containing pendant sulfonic and/or carboxylic acid groups entrapped within and highly dispersed throughout a network of metal oxide. Similar microcomposites can be used in the present invention.

The $H_2O_2$-producing catalyst comprises a polymer-encapsulated combination of a noble metal and an ion-exchange resin. The combination of a noble metal and an ion-exchange resin is referred to as a "noble metal catalyst." By "encapsulated," we mean that the both the noble metal and the ion-exchange resin are contained within and are surrounded by a layer of polymer. Because ion-exchange resins are typically supplied as beads of various sizes (e.g., from about 10 µm to about 2 mm), the noble metal catalyst typically has a particle size similar to that of the ion-exchange resin used. Thus, the polymer-encapsulation involves entrapping the noble metal and the ion-exchange resin within a polymeric coating.

Polymers suitable for use in making $H_2O_2$-producing catalyst include natural or synthetic organic polymers (containing carbon atoms) made by addition or condensation polymerizations. Generally, the polymers are homopolymers or random and block copolymers produced by free-radical, ionic, coordination, or condensation polymerization of one or more polymerizable monomers. Examples include polystyrenics, polyolefins, polyethers, polyureas, polyacrylics, polyurethanes, polyesters, polyamides, polysiloxanes, polysaccharides, polypeptides, poly-nucleotides, and the like, and mixtures thereof. Preferred are polystyrenics, polyolefins, and mixtures thereof. Particularly preferred is polystyrene. The polymers can be generated by bulk, solution, suspension, or emulsion polymerizations. The polymers can be hydrocarbons, or they can incorporate functional groups such as halogens, hydroxyl, amine, phosphine, phosphine oxide, arsine, sulfur, sulfur oxides, alkoxy, silane, siloxy, carboxy, or the like.

The order in which the noble metal addition to the ion-exchange resin and the polymer-encapsulation are carried out is not critical, as long as both the ion-exchange resin and the noble metal are essentially enveloped within a thin layer of polymer. In one preferred approach, a noble metal is added to an ion-exchange resin to form a noble metal catalyst prior to its encapsulation. In another approach, an ion-exchange resin is encapsulated within a polymer to produce a polymer-encapsulated ion-exchange resin, and a transition metal is added to the polymer-encapsulated ion-exchange resin afterward. In this case, the noble metal compounds (e.g., palladium halides, palladium acetate) or complexes (e.g., palladium(II) tetraammine bromide, tetrakis(triphenyl-phosphine) palladium(0)) diffuse through the polymer layer and deposit on the ion-exchange resin, thus both the ion-exchange resin and the transition metal are encapsulated in the finally obtained $H_2O_2$-producing catalyst. In yet another preferred approach, addition of the noble metal to the ion-exchange rein and polymer-encapsulation are performed in a single step. In one example, a solution containing a noble metal source and a monomer (e.g., styrene) or a mixture of monomers, an initiator, and/or other components (e.g., an organic solvent) is mixed with a slurry containing an ion-exchange resin and water. The noble metal is added to the ion-exchange resin as the polymerization of the monomer occurs, resulting in a polymer-encapsulated noble metal catalyst. In another example, evaporating the solvent from a slurry containing an ion-exchange resin and a solution of a noble metal source and a dissolved polymer can provide a polymer-encapsulated noble metal catalyst.

There are many suitable ways to encapsulate a noble metal catalyst within a polymer. Suitable techniques include, for example, spray-drying, spray-chilling, spray-coating, phase separation and coascervation, injection treatment coating, fluid bed coating, dry-on-dry coating, melt extrusion, vapor deposition, in-situ polymerization, including in-situ interfacial polymerization, and the like. These and other microencapsulation techniques are described in the introductory chapter of *Microcapsules and Nanoparticles in Medicine and Pharmacy*, M. Donbrow, Ed., pp. 1-14, and references cited therein, and in G. Beestman, "Microencapsulation of Solid Particles," in *Controlled-Release Delivery Systems for Pesticides* (1999), H. Scher, Ed., pp. 31-54. See also U.S. Pat. No. 6,156,245.

In-situ polymerization is one preferred technique. The noble metal catalyst is suspended in a reaction medium containing monomer(s), an initiator, and other components (e.g., a crosslinking reagent), and polymerization proceeds to give the polymer-encapsulated noble metal catalyst. The monomers can be hydrophilic (e.g., N-vinylpyrrolidone, N,N-dimethylacryl amide), hydrophobic (e.g., styrene), or a combination of these. Suitable techniques include bulk, emulsion, suspension, and interfacial polymerizations. The $H_2O_2$-producing catalyst can be prepared in such a manner. As an example, styrene or a mixture of styrene and other ethylenic monomer(s) may be polymerized in an aqueous suspension of a noble metal catalyst.

Polymer encapsulation by phase separation/coascervation is another preferred technique. A suitable approach with polystyrene as the polymer encapsulant is illustrated by Kobayashi et al. (see *Chem. Communt.* (2003) 449 and references cited therein; *Angew. Chem., Int. Ed.* 40 (2001) 3469; *J. Am. Chem. Soc.* 120 (1998) 2985). In a particularly convenient coascervation approach taught by Kobayashi for encapsulating a palladium compound, polystyrene is dissolved in warm cyclohexane. Tetrakis(triphenylphosphine)palladium(0) is dissolved in the mixture. Upon slow cooling to 0° C., phase separation and capsule formation occur. Hexane is added to harden the microcapsules, which are then isolated, washed, and dried. Similarly, a noble metal catalyst is mixed with a solution of a polymer (e.g., polystyrene, polyisobutylene) in a solvent. Upon cooling to a lower temperature and/or the addition of another solvent to reduce the solubility of the polymer in the solvent mixture, phase separation occurs and a polymer-encapsulated noble metal catalyst is obtained.

One interfacial method is illustrated by Ley et al. (see *Chem. Commun.* (2002) 1132 and 1134; and *Chem. Commun.* (2003) 678) in the preparation of polyurea-encapsulated transition metals. In Ley's example, an organic phase containing polymerizable monomers and the transition metal source is dispersed within an aqueous phase that contains emulsifiers and/or stabilizers. Polymerization occurs at the interface to form microcapsule walls. A polyurea-encapsulated noble metal catalyst is analogously prepared by substituting a noble metal catalyst for the transition metal source. For another example of in-situ polymerization to generate microcapsules, see *Adv. Powder Technol.* 13(2002) 265.

Polymer-encapsulation of the noble metal catalyst can improve the performance (e.g., rate, selectivity, catalyst life) and filterability and also should reduce the leaching of the noble metal into reaction mixtures. Particularly where the cost of the metal is high (e.g., Pd), reducing metal loss can result in significant financial advantages.

The $H_2O_2$-producing catalyst may be further treated by techniques such as heat treatment, oxidation, reduction, and the like prior to use in hydrogen peroxide production. For example, the catalyst may be reduced under an atmosphere containing hydrogen. The encapsulant polymer and the noble metal may undergo physical or chemical changes as a result of such treatment. For example, an unsaturated polymer encapsulant (e.g., polybutadiene) may be hydrogenated by hydrogen treatment while the noble metal may be reduced to its lower oxidation states.

The $H_2O_2$-producing step uses a solvent. Suitable solvents are liquid under reaction conditions. They include, e.g., oxygen-containing hydrocarbons such as alcohols, aromatic and aliphatic solvents such as toluene and hexane, chlorinated aromatic and aliphatic solvents such as chlorobenzene and methylene chloride, nitriles such as acetonitrile, carbon dioxide, and water. Suitable oxygenated solvents include carbon dioxide, water, and oxygen-containing hydrocarbons such as alcohols, ethers, esters, ketones, and the like, and mixtures thereof. Preferred oxygenated solvents include water, lower aliphatic $C_1$-$C_4$ alcohols such as methanol, ethanol, isopropanol, and tert-butanol, and mixtures thereof. Fluorinated alcohols can be used.

The $H_2O_2$-producing step uses oxygen and hydrogen. Although any sources of hydrogen and oxygen can be used, molecular oxygen ($O_2$) and molecular hydrogen ($H_2$) are preferred. The molar ratio of hydrogen to oxygen ($H_2:O_2$) used is preferably within the range of 1:10 to 10:1.

In addition to oxygen and hydrogen, an inert gas may be used. The inert gas can help to keep the oxygen and hydrogen levels in the reaction mixture outside the explosive limits. Suitable inert gases are helium, argon, nitrogen, methane, ethane, propane, carbon dioxide, and the like, and mixtures thereof.

The $H_2O_2$-producing step may be performed using a continuous flow, semi-batch, or batch mode. The catalyst may be used in the form of slurry or fixed bed. It is preferred to operate at a total pressure within the range of 1 to 200 bars. The reaction is performed at a temperature effective to produce the desired amount of hydrogen peroxide, preferably at temperatures within the range of 0° C. to 120° C., more preferably from 20° C to 80° C.

It may be advantageous to use a hydrogen peroxide stabilizer in hydrogen peroxide production to minimize hydrogen peroxide decomposition. Suitable stabilizers include inorganic and organic acids and their salts, chelating agents, and the like, and mixtures thereof. Examples of hydrogen peroxide stablizers are nitric acid, sulfuric acid, phosphoric acid, hydrochloric acid, hydrobromic acid, pyrophosphoric acid, aminotri(methylenephosphonic acid), 1-hydroxyethylidene-1,1-diphosphonic acid, and ethylenediaminetetra(methylenephosphonic acid). The stabilizer is typically added within the range of 0.1 ppm to 10wt. %.

A hydrogen peroxide solution is obtained in the $H_2O_2$-producing step. Where the reaction is performed in a slurry reactor, the $H_2O_2$-producing catalyst is preferably removed from the reaction mixture using techniques well known in the art, such as decantation, centrifugation, filtration, and the like to obtain a hydrogen peroxide solution. If the $H_2O_2$-producing catalyst is used in fixed bed, then the product mixture usually contains very little catalyst, thus additional separation operation is not necessary. Preferably the hydrogen peroxide solution contains less than 10 wt. %, more preferably less than 2 wt. % of the total catalyst used. The solution may contain hydrogen peroxide stabilizers, non-reacted hydrogen and oxygen, and the like. It may be desirable that at least a portion of gases from the hydrogen peroxide production step, such as hydrogen, oxygen, and inert gases, is removed. In some cases it may be desirable to remove a portion of the solvent to generate a more concentrated hydrogen peroxide solution.

Oxidation Step

The process of the invention also includes an oxidation step which comprises reacting an organic compound with the hydrogen peroxide solution in the presence of an oxidation catalyst.

The oxidation catalyst is any catalyst capable of catalyzing the oxidation of an organic compound with hydrogen peroxide. The oxidation catalyst typically includes a transition metal. Suitable transition metals are Group 3 to 11 metals.

The first row of these metals includes Sc, Ti, V, Cr, Mn, Fe, Co, Ni, and Cu. The transition metal may be present in any suitable oxidation state as long as it is capable of catalyzing the reaction. Examples of suitable oxidation catalysts are: transition metal salts (e.g., $FeCl_3$, $Cr_2(SO_4)_3$), transition metal complexes (e.g., titanium(IV) tetra(isopropoxide), titanium bis(isopropoxide) acetylacetonate, methylrhenium (VII) trioxide), transition metal oxides (e.g., titania, tungsten (VI) oxide, niobium oxide), supported transition metal oxides (e.g., titanium oxide supported on silica, alumina, or other supports), mixed metal oxides (e.g., titania/silica, vanadia/silica), transition metal zeolites (e.g., titanium silicates, vanadium silicates), heteropolyacids (see, e.g., the catalyst described in *Applied Catalysis A: General*, 250(2) (2003) 239), and the like, and mixtures thereof. The oxidation catalyst may be soluble, partially soluble, or essentially insoluble in the reaction mixture under the reaction conditions.

Preferably, the oxidation catalyst comprises a transition metal zeolite. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the organic compound to be oxidized. For example, it is preferred to use a relatively small pore zeolite such as a transition metal silicalite if the organic compound is a lower aliphatic olefin such as ethylene, propylene, or 1-butene.

Titanium silicates (titanosilicates) are suitable oxidation catalysts. Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and the like, and mixtures thereof, may be present in the lattice. The amount of impurities is preferably less than 0.5 wt. %, more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev. Sci. Eng.*, 39(3) (1997) 209). Examples of these include TS-1 (titanium silicalite-1, a titanium silicalite having an MFI topology analogous to that of the ZSM-5 aluminosilicate), TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use.

In addition to a titanium zeolite, the oxidation catalyst may contain other components including titania, zirconia, niobia, silica, alumina, silica-alumina, titania-silica, zirconia-silica, niobia-silica, and mixtures thereof as part of the catalyst. For example, a titanium zeolite may be formed into particles (e.g., spay-dried, palletized, etc) by itself or in combination with a binder (e.g., silica, alumina, silica-alumina, titania-silica, and the like).

The oxidation step may be performed using a continuous flow, semi-batch, or batch mode. It is advantageous to work at a pressure of 1-200 bars and at temperatures in the range of 0-250° C., more preferably, 20-200° C. Additional solvent and/or inert gas may be added to the reaction mixture. Suitable and preferred solvents and inert gases for the $H_2O_2$-producing step are applicable.

It may be advantageous to use a buffer in the oxidation step. The buffer may typically be added to the solvent to form a buffer solution, or to the hydrogen peroxide solution. The buffer may also be added directly to the oxidation reaction mixture. The buffer is employed in the reaction to improve the reaction rate and/or selectivities. Buffers useful in this invention include any suitable salts of oxyacids, the nature and proportions of which in the mixture, are such that the pH of their solutions may preferably range from 3 to 10, more preferably from 4 to 9, and most preferably from 5 to 8. Suitable salts of oxyacids contain an anion and cation. The anion may include phosphate, carbonate, bicarbonate, sulfate, carboxylates (e.g., acetate), borate, hydroxide, silicate, aluminosilicate, and the like. The cation may include ammonium, alkylammonium (e.g., tetraalkylammoniums, pyridiniums, and the like), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of buffer in the solvent is from 0.0001 M to 1 M, preferably from 0.0005 M to 0.3 M. The buffer useful in this invention may include ammonium hydroxide which can be formed by adding ammonia gas to the reaction system. For instance, one may use a pH=12-14 solution of ammonium hydroxide to balance the pH of the reaction system. More preferred buffers include alkali metal phosphate, ammonium phosphate, and ammonium hydroxide.

A variety of organic compounds may be oxidized by the present process. Examples of organic compounds include olefins, alkanes, arenes, alcohols, aldehydes, ketones, thioethers, and the like.

In one preferred oxidation process, the organic compound is an olefin, and the oxidation product is an epoxide. Suitable olefins include any olefin having at least one carbon-carbon double bond, and generally from 2 to 60 carbon atoms. Preferably the olefin is an acyclic alkene of from 2 to 30 carbon atoms; the process is particularly suitable for epoxidizing $C_2$-$C_6$ olefins. More than one double bond may be present in the olefin molecule, as in a diene or triene. The olefin may be a hydrocarbon or may contain functional groups such as halogen, carboxyl, hydroxyl, ether, carbonyl, cyano, or nitro groups, or the like. In a particularly preferred process, the olefin is propylene and the epoxide is propylene oxide. Olefins may also be oxidized to other products including aldehydes, ketones, and carboxylic acids.

Alkane oxidation to alcohols, ketones, or other oxygenated products is another preferred oxidation process of the invention. The process is valuable because the oxygenated products are usually more valuable than nonfunctionalized hydrocarbons. Suitable alkanes include those containing halogen, oxygen, aryl groups, and the like, and mixtures thereof. Examples of alkanes include, e.g., ethane, propane, n-butane, isobutane, toluene, ethylbenzene, and cumene.

Other oxidation reactions include, e.g., oxidations of arenes to phenols, phenols to catechols, ketones to esters or lactones, thioethers to sulfoxide and/or sulfones, ammoximation of aldehydes or ketones in the presence of ammonia or an amine to make oximes (e.g., the conversion of cyclohexanone to cyclohexanone oxime).

The following examples merely illustrate the invention. Those skilled in the art will recognize many variations that are within the spirit of the invention and scope of the claims.

COMPARATIVE EXAMPLE 1

Pd/A36 Catalyst

Amberlyst 36 resin (A36, an acidic resin obtained from Rohm & Haas) (50.5 g) is washed with methanol (100 g) in a beaker under gentle agitation. The methanol is then decanted. The methanol washing step is repeated six times. To a suspension containing the washed A-36 resin and methanol (100 g), a palladium acetate solution (1.71 g of $Pd(OAc)_2$ in 70 g acetone) is added with mixing at room temperature. After 30 min, the solid is filtered and washed with methanol (100 g)

and dried in a vacuum oven at 60° C. to constant weight. The dried solid (Catalyst A, 46.5 g) contains 1.9 wt. % Pd.

EXAMPLE 2

Polystyrene-Encapsulated Pd/A36 Catalyst

Into a 2-oz crown cap bottle containing a solution of styrene (13 g) and 2,2'-azobis(isobutyronitrile) (AIBN, 0.15 g), a aqueous poly(vinyl alcohol) solution (0.15 wt. %, 120 g) and Catalyst A (30 g) from Example 1 are charged. After being purged with nitrogen, the bottle is capped and the suspension polymerization is effected by end-over-end agitation in an oil bath at 70° C. for 3 h, followed by another 3 h at 90° C. After cooling to room temperature, the polymer-encapsulated catalyst is filtered, washed twice with deionized water, and dried in a vacuum oven at 60° C. to constant weight. The product (Catalyst B) contains 1.1 wt. % Pd.

EXAMPLE 3

Hydrogen Peroxide Production

The tests are conducted in a 450-mL multi-tube Parr reactor. Five test tubes in the reactor share the same gas phase. Each test tube has a magnetic stirring bar and all bars stir at the same rate. Test tubes 1, 2 and 5 are each charged with Catalyst B (10 mg). Test tubes 3 and 4 are each charged with 5.6 mg of Catalyst A (5.6 mg). The catalyst in each test tube contains about 0.1 mg of Pd. After a mixture of methanol/water (70/30 by weight, 5.6 g) is added to each test tube, the reactor is closed and flushed with nitrogen. After the reactor contents are heated to 30° C., the reactor is charged with hydrogen to 100 psig, and then charged with a mixture of oxygen (4 mol %) in nitrogen to 1400 psig. The reaction mixture in each test tube is stirred magnetically at 30° C. for 1 h before it is cooled to room temperature. The concentration of hydrogen peroxide in each solution is determined by liquid chromatography (LC) and listed in Table 1.

Table 1 shows that the process employing a polymer-encapsulated Pd/A36 catalyst gives higher yields of hydrogen peroxide than a similar process performed with the same amount of Pd on a Pd/A36 catalyst which is not encapsulated by a polymer.

TABLE 1

Hydrogen Peroxide Production

| Test | Catalyst | Catalyst Composition | Hydrogen Peroxide [ppm] |
|---|---|---|---|
| 1 | B | 1.04 wt. % Pd/A36/PS (10 mg) | 1407 |
| 2 | B | 1.04 wt. % Pd/A36/PS (10 mg) | 1154 |
| 3* | A | 1.9 wt. % Pd/A36 (5.6 mg) | 611 |
| 4* | A | 1.9 wt. % Pd/A36 (5.6 mg) | 717 |
| 5 | B | 1.04 wt. % Pd/A36/PS (10 mg) | 1413 |

*Comparative test.

EXAMPLE 4

Epoxidation of Propylene

An autoclave equipped with a stirrer is charged with a 5 wt. % hydrogen peroxide solution in methanol and water (prepared by mixing commercially available 30 wt. % aqueous hydrogen peroxide and methanol, 40 g), TS-1 (150 mg), and propylene (21 g). The TS-1 catalyst contains 2.2 wt. % Ti. The reactor is heated to 50° C. and kept at 50° C. for 0.5 h. The reaction mixture is analyzed by gas chromatography (GC). LC analysis shows 93% hydrogen peroxide conversion. The GC shows the formation of propylene oxide (PO), propylene glycol (PG), and methoxypropanols (PMs) in 94, 0.5, and 5.5 mol. % selectivities, respectively. Calculations are performed as follows. POE (mole)=Total PO equivalents formed=moles of PO+moles of PO units in PO derivatives such as PG and PM. PO selectivity=(moles of PO)/(moles of POE)×100. PG selectivity=(moles of PG)/(moles of POE)×100. PM selectivity=(moles of PMs)/(moles of POE)×100.

It is expected that repeating the procedure of Example 4 except with a hydrogen peroxide solution produced by the reaction of hydrogen and oxygen in the presence of a $H_2O_2$-producing catalyst (e.g., Catalyst B of Example 2) should give similar results in the epoxidation of propylene.

EXAMPLE 5

Epoxidation of Propylene in the Presence of Buffer

The procedure of Example 4 is repeated except that an ammonium phosphate buffer is added (540 ppm, pH=6). Reaction time is 0.5 h at 50° C. and LC analysis shows 38% hydrogen peroxide conversion. PO, PG, and PM selectivities are 99, <0.1, and 0.3 mol. % respectively.

EXAMPLE 6

Oxidation of Propane

The autoclave equipped with a stirrer is charged with 30 wt. % aqueous hydrogen peroxide (0.4 g), methanol (18 g), TS-1 (200 mg), and propane (8 g). The TS-1 catalyst contains 2.2 wt. % Ti. The reactor is heated to 60° C. and kept at 60° C. for 1.75 h. GC of the reaction mixture shows 0.36 wt. % isopropanol and 0.1 wt. % acetone.

It is expected that repeating the procedure of Example 6 except with a hydrogen peroxide solution produced by the reaction of hydrogen and oxygen in the presence of a $H_2O_2$-producing catalyst (e.g., Catalyst B of Example 2) should give similar results in the oxidation of propane.

We claim:
1. A process which comprises:
 (a) reacting hydrogen and oxygen in a solvent in the presence of a $H_2O_2$-producing catalyst comprising a polymer-encapsulated combination of a noble metal and a sulfonic acid polystyrene resin having 1 to 10 equivalents per kilogram of functional groups, to obtain a hydrogen peroxide solution; and
 (b) reacting an olefin with the hydrogen peroxide solution in the presence of an oxidation catalyst to produce an epoxide.
2. The process of claim 1 wherein the noble metal is selected from the group consisting of palladium, platinum, gold, rhenium, silver, and mixtures thereof.
3. The process of claim 1 wherein the noble metal is palladium.
4. The process of claim 1 wherein the polymer is selected from the group consisting of polystyrenics, polyolefins, and mixtures thereof.
5. The process of claim 1 wherein the polymer is polystyrene.
6. The process of claim 1 wherein the $H_2O_2$-producing catalyst further comprises a component selected from the group consisting of carbon, titania, zirconia, niobia, silica, alumina, silica-alumina, titania-silica, zirconia-silica, niobia-silica, and mixtures thereof.

7. The process of claim 1 wherein step (a) is performed in the presence of a hydrogen peroxide stabilizer.

8. The process of claim 1 wherein the solvent is an oxygenated solvent.

9. The process of claim 1 wherein the solvent is selected from the group consisting of alcohols, ethers, esters, ketones, carbon dioxide, water, and mixtures thereof.

10. The process of claim 1 wherein step (b) is performed in the presence of a buffer.

11. The process of claim 1 wherein the oxidation catalyst is a titanium zeolite.

12. The process of claim 11 wherein the titanium zeolite is TS-1.

13. A process which comprises:
 (a) reacting hydrogen and oxygen in a solvent in the presence of a $H_2O_2$-producing catalyst comprising a polymer-encapsulated combination of palladium and a sulfonic acid polystyrene resin, to obtain a hydrogen peroxide solution; and
 (b) reacting propylene with the hydrogen peroxide solution in the presence of a titanium zeolite to produce propylene oxide.

14. The process of claim 13 wherein the titanium zeolite is TS-1.

* * * * *